(12) United States Patent
Hanson et al.

(10) Patent No.: US 7,722,676 B2
(45) Date of Patent: May 25, 2010

(54) ARTICULATING IMPLANT SYSTEM

(75) Inventors: Shaun Hanson, Phoenixville, PA (US);
Graham J. W. King, London (CA);
Stuart D. Patterson, Winter Haven, FL (US); Alan Taylor, Memphis, TN (US);
James A. Johnson, London (CA)

(73) Assignee: Wright Medical Technology, Inc., Arlington, TN (US)

( * ) Notice: Subject to any disclaimer, the term of this patent is extended or adjusted under 35 U.S.C. 154(b) by 1056 days.

(21) Appl. No.: 10/772,129

(22) Filed: Feb. 4, 2004

(65) Prior Publication Data
US 2004/0230312 A1    Nov. 18, 2004

Related U.S. Application Data

(60) Provisional application No. 60/445,474, filed on Feb. 5, 2003.

(51) Int. Cl.
*A61F 2/42* (2006.01)
(52) U.S. Cl. .................................... 623/21.12
(58) Field of Classification Search ............. 623/21.12, 623/21.11, 21.13, 21.14, 23.42, 23.44, 23.5, 623/23.57, 23.41, 18.11
See application file for complete search history.

(56) References Cited

U.S. PATENT DOCUMENTS 3,745,590 A    7/1973    Stubstad
5,108,444 A    4/1992    Branemark
5,782,926 A    7/1998    Lamprecht
5,938,699 A    8/1999    Campbell
5,951,604 A    9/1999    Scheker
6,027,534 A *  2/2000    Wack et al. .............. 623/20.12
6,302,915 B1   10/2001   Cooney et al.

FOREIGN PATENT DOCUMENTS

FR    2660856      4/1990
WO    WO01/01892 A1    1/2001
WO    WO01/70138 A1    9/2001

OTHER PUBLICATIONS

International Search Report, PCT International Search Report mailed Jul. 23, 2004 for PCT/US2004/003517 (filed Feb. 5, 2004).
International Preliminary Report on Patentability mailed Aug. 18, 2005 for PCT/US2004/003517 (filed Feb. 5, 2004).

* cited by examiner

*Primary Examiner*—Eduardo C Robert
*Assistant Examiner*—David Comstock

(57) ABSTRACT

An articulating implant system is provided for fixation to a bone. The articulating implant system includes a fixation component for fixation to the bone and an articulating member for articulating against bone or cartilage. Specifically, a modular ulnar implant is provided in accordance with the articulating implant system of the present invention wherein the fixation component is a stem for insertion into the intramedullary canal of the distal ulna and the articulating member is a head for articulating with the radial sigmoid notch.

20 Claims, 3 Drawing Sheets

ARTICULATING IMPLANT SYSTEM

RELATED APPLICATIONS

This application claims priority to U.S. Provisional Patent Application Ser. No. 60/445,474, filed Feb. 5, 2003.

FIELD OF THE INVENTION

The present invention relates to an articulating implant system for fixation to a bone. Specifically, the present invention provides an articulating implant system for replacing the distal ulna.

BACKGROUND OF THE INVENTION

Both the proximal and distal radioulnar joints are synovial joints. The proximal joint lies between the head of the radius and the radial notch of the ulna. The distal radioulnar joint is separated from the wrist by an articular disc that extends from the base of the ulnar styloid process to the radius.

The distal radioulnar joint is a pivot-joint formed between the head of the ulna and the ulnar notch on the lower end of the radius. The articular surfaces are connected together by the volar radioulnar ligament, the dorsal radioulnar ligament, and the articular disk. The volar radioulnar ligament is a narrow band of fibers extending from the anterior margin of the ulnar notch of the radius to the front of the head of the ulna. The dorsal radioulnar ligament extends between corresponding surfaces on the dorsal aspect of the articulation. The articular disk is triangular in shape, and is placed transversely beneath the head of the ulna, binding the lower ends of the ulna and radius firmly together. Its periphery is thicker than its center, which is occasionally perforated. It is attached by its apex to a depression between the styloid process and the head of the ulna; and by its base, which is thin, to the prominent edge of the radius, which separates the ulnar notch from the carpal articular surface. Its margins are united to the ligaments of the wrist-joint. Its upper surface, smooth and concave, articulates with the head of the ulna, forming an arthrodial joint; its under surface, also concave and smooth, forms part of the wrist-joint and articulates with the triangular bone and medial part of the lunate. Both surfaces are clothed by synovial membrane; the upper, by that of the distal radioulnar articulation, the under, by that of the wrist.

The radius articulates in pronation and supination on the distal ulna. The ulna, a relatively straight forearm bone linked to the wrist, translates dorsal-palmarly to accept the modestly bowed radius. Since the sigmoid fossa socket in most wrists is relatively flat, ligaments are required to support the distal ulna. These ligaments include the triangular fibrocartilage (TFC), the extensor carpi ulnaris (ECU) subsheath, and the ulnar collateral ligament complex. The stabilizing elements of the triangular fibrocartilage (TFC), extensor carpi ulnaris (ECU) subsheath, and the ulnar collateral complex are well recognized along with the importance of a distal ulna component (ulnar head) for transfer of compressive loads between the ulnar carpus and the distal ulna across the distal radioulnar joint. The distal radioulnar joint shares loading forces that occur with forearm rotation and gripping. The arc of pronation and supination averages 150 to 160 degrees with the most useful portion being between 80 degrees pronation and 45 degrees supination.

One of the most common fractures in humans is fracture of the distal radius. Inherent bony instability, soft tissue damage, and frequent associated injuries make the distal radius fractures very difficult to treat. Distal radius fractures are usually caused by a fall on an outstretched hand. When a person falls on an outstretched hand, the hand suddenly becomes rigid, and the momentum from the fall will cause both a twisting force and a compressing force on the forearm. The kind of injury these forces are likely to cause depends on the age of the person who is injured. In children, and in older adults, such a fall is likely to result in a fracture of the radius. Distal radius fractures may also result from direct trauma such as might occur during an auto accident.

There are several types of fractures. A non-displaced fracture is one in which the bone cracks and the broken pieces stay in alignment. A torus or ripple fracture bends the back of the radius away from the growth plate. A displaced fracture is one in which the bone breaks in two or more pieces that move out of alignment. Such a break may be extremely painful and produces a deformity that is easily seen. An open or compound fracture is one in which the ends of the bone are displaced and pierce the skin. In these cases, there is a significant risk of infection.

For displaced broken bones to heal properly and without serious complications, they need to be set and held in place for the body to repair and replace the damaged bone. The process usually takes between 4 and 12 weeks. Some fractures may be set without surgery, the bones being held in place first with a splint and then, after healing has started, with a cast. If the bones are seriously displaced, however, or if there is damage that needs to be repaired, surgery may be needed and the bones may need to be held together with pins or wire.

Closed treatment methods including casting, pins and plaster, and external fixation have frequently yielded unsatisfactory results. Treatment using formal open reduction and internal fixation with the conventional plate system, when achieving anatomic reduction and early mobilization, has produced some promising results. The value of immediate mobilization of the injured joints is clear.

With distal radial fractures, muscles may gradually weaken from lack of use during bone healing. A patient may need physical therapy in order to regain proper use of the wrist.

Ligament disruption, ulnar styloid fractures, and fractures into the distal radioulnar joint are common occurrences following fractures of the distal radius and other rotational instability injuries of the forearm. Fracture or dislocation involving the distal radioulnar joint often results in a loss of forearm rotation related to either instability or incongruity between the sigmoid fossa of the distal radius and the ulnar head. A variety of different fractures involving the distal radius may cause this condition including the Colles' fracture and the Galeazzi fractures.

When there is loss of stability of the distal radioulnar joint, there is subsequent weakness in grip and pinch as well as potential loss of forearm rotation. Instability may also be associated with either an injury to the triangular fibrocartilage or to the ulnar styloid. When instability is present, a number of ligament reconstructive procedures have been devised to assist in treating the unstable distal ulna. Unfortunately, ligament reconstruction of the distal ulna is often incomplete in restoring stability, and joint replacement is often necessary.

Where there is an incongruity of the joint surface involving either the articulation of the ulnar head with the sigmoid fossa of the distal radius, or if there is a significant ulnar impaction syndrome between the distal articular surface of the head of the ulna and the ulna carpus, a joint replacement may be necessary. Specifically, this may include either joint replacement of the distal ulna or operative procedures designed to shorten the ulna or resect all or part of the distal ulna (i.e. Darrach, Bowers, or matched resection procedures).

Implants or prostheses are employed for restoring damaged upper and lower extremity bones such as fingers, wrists, elbows, knees and ankles of human patients. These prostheses are especially useful in the reconstruction of joints which, for example, have been damaged by pathological conditions such as rheumatoid arthritis, degenerative arthritis, aseptic necrosis, and for treating trauma which may have a debilitating effect on articular joints.

There are three types of arthroplasties: 1) unconstrained, 2) semi-constrained and 3) fully constrained. A common flaw with all of these current joint replacement designs is the inability to reconstruct and re-attach the replaced joint's vital native capsular and ligamentous restraints, which dictate, in large measure, the behavior and stability of the joint (i.e., its kinematics).

The primary reasons for wrist replacement surgery are to relieve pain and to maintain function in the wrist and hand. The primary indications, therefore, for reconstruction of the distal radioulnar joint by prosthetic replacement (ulnar head replacement only) are generally related to a fracture of the distal ulna or a fracture extending into the distal radioulnar joint producing post-traumatic arthritis. Degenerative arthritis from other causes is also a primary indication. This is considered if there is associated arthritis and an ulnar shortening procedure is contraindicated. Osteoarthritis, the most common form of arthritis, results from a gradual wearing away of the cartilage covering on bones. A third condition for primary ulna replacement is rheumatoid arthritis with a painful and unstable distal radioulnar joint. Rheumatoid arthritis is a chronic inflammatory disease of the joints that results in pain, stiffness and swelling. Rheumatoid arthritis usually affects several joints on both the right and left sides of the body. Both forms of arthritis may affect the strength of the fingers and hand, making it difficult to grip or pinch. In some cases, fusing the wrist bones together will reduce or eliminate pain and improve grip strength. However, if the bones are fused together, the ability of the wrist to move and bend is lost. Wrist replacement surgery may enable retention or recovery of wrist movements. In these situations, prosthetic replacement of the distal ulna with soft tissue advancement may be beneficial.

A distal ulnar prosthesis is also suitable to correct a previous resection of the distal ulna that has failed. Such will be the case for both partial resection of the joint articular surface and complete resection of the distal ulna. When faced with failed distal ulna resection, one has options towards reconstruction without restoring the distal radioulnar joint (DRUJ). For example, a failed distal ulna may be corrected by a pronator quadratus interposition, or, if there has been only a partial resection, a fusion of the distal radioulnar joint combined with a proximal pseudarthrosis (Suave-Kapandji procedure). These procedures, however, do not restore the normal DRUJ function of motion or load transfer and may be associated with instability of the distal ulna and proximal impingement of the ulna on the distal radius. In these cases, a distal ulna prosthesis is generally preferable. A distal ulnar prosthesis is also suitable to correct a previous prosthetic replacement such as a silicone ulnar head replacement which has failed.

A distal ulnar prosthesis attachable to a soft tissue pocket including the triangular fibrocartilage, ECU subsheath, and ulnar collateral ligament complex to thereby maintain distal radioulnar joint stability, which aligns anatomically with the sigmoid fossa of the distal radius and is isosymmetric with the anatomic center of rotation of the forearm, and that allows for a normal forearm rotation of approximately 150-170 degrees would be desirable. More specifically, it would be desirable to have such a modular distal ulnar prosthesis wherein there is no risk of separation of the two components (the stem and the head) due to biomechanical forces from the tissues attached by suture to the implant.

SUMMARY OF THE INVENTION

The present invention is directed to an articulating implant system for fixation to a bone. The implant system comprises two components: a fixation component and an articulating component.

The fixation component has first and second ends. The first end of the fixation component is configured for fixation to a bone. This may be, for example, a stem. The second end of the fixation component is configured for operative attachment to the articulating component. Suture attachment means are provided at or near the second end of the fixation component. This may be, for example, by provision of holes for receiving sutures, the holes positioned through an extension provided at the second end of the fixation component.

The articulating component is configured for articulating against bone or cartilage. Optionally, an area of the articulating component may have a porous surface for ingrowth. This area would preferably be near the suture attachment means of the fixation component. A connecting taper means may be provided at a first end thereof. The articulating component is configured for operative attachment to the fixation component. This may be done by, for example, a Morse taper. It is preferable that the suture attachment means of the fixation component cooperate with the articulating component such that the attachment means is provided at a suitable location near the articulating surface.

In one embodiment, an extension is provided at the second end of the fixation component. Suture holes are provided at both the distal and the proximal ends of the extension. A bore is provided through the articulating component such that the extension of the fixation component passes therethrough, the suture hole provided at the distal end of the extension extending through the bore, the suture holes provided at the proximal end of the extension failing to pass through the bore. Thus, upon assembly, the implant system has attachment means at both ends of the articulating component.

The articulating implant system of the present invention is particularly suited to a modular ulnar implant for implantation after a resection of the distal ulna. In the embodiment of a modular ulnar implant, the fixation component is a stem and the articulating component is a head. Generally, the modular ulnar implant comprises an eccentric head and a stem, the stem having suture holes for receiving sutures to anchor the implant to soft tissues that are exposed after resection of the distal ulna. Preferably, the stem attaches to the head via a morse taper. These soft tissues include the ulna collateral capsule, the triangular fibrocartilage, and the extensor carpi ulnaris subsheath.

The head is offset from the stem, is triangulated to reproduce normal anatomy, and has an approximately 200° arc for mating with the radial sigmoid notch. The head includes a bore extending completely therethrough for receiving an extension from the stem. Additionally, the head may include a drainage hole and instrument interface on its distal surface to allow effective in vivo assembly and rotational positioning. Optionally, the head is covered, at least near the triangulated portion, with an ingrowth coating to promote ingrowth with the soft tissues.

The stem has first and second ends. The first stem end is configured for fixation to a bone, is tapered to match the ulnar canal anatomy and is preferably fluted for effective fixation in the canal. The second stem end is configured for operative attachment to the head. The stem includes a platform near the head interface at the second stem end to prevent subsidence into the ulnar canal. The stem includes suture holes for receiving sutures to anchor the implant to soft tissues. The suture holes anchor the implant to the triangular soft tissues. A stem extender collar may be used to add additional resection height. The stem may include an instrument interface for positioning control.

In one embodiment, the stem includes an extension at the second end, preferably centrally located on a morse taper. The extension is configured for receipt by the bore in the head. At least one suture hole is provided at the distal end of the extension for receiving sutures, the suture hole being accessible after the head has been placed on the stem. Suture holes may also be provided on the platform near the stem second end, near the head interface. In this embodiment, the suture holes in the platform and in the extension anchor the implant to the triangular soft tissues.

The articulating implant system allows for attachment of tissues near a surface or location of an articulating component without attaching the suture to that component. This allows independent rotation and orientation of the articulating component, a head in a modular ulnar implant system, with respect to the tissue suture attachment. Forces or constraints of the tissue attachment do not affect the orientation or behavior of the articulating component. The implant also allows for more versatility of the suture attachment by not being constrained to the non-articulating area of the articulating component.

In the case of a typical ulnar implant, there is risk of component separation due to the rotation of the implant relative to the surrounding tissue that could be suture attached to the implant. With the present design, the risk of component separation is eliminated. Using the modular ulnar implant of the invention, there is no risk of separation of the two components (the stem and the head) due to biomechanical forces from the tissues attached by suture to the implant. By having the suture attachment means on the fixation component, a stem in a modular ulnar implant system, forces from the suture tissue attachment are transferred directly through the fixation component to the bone and not through the connection of the articulating component to the fixation component.

DETAILED DESCRIPTION OF THE INVENTION

The present invention is directed to an articulating implant system for fixation to a bone. The implant system comprises two components: a fixation component and an articulating component.

Figure 1:
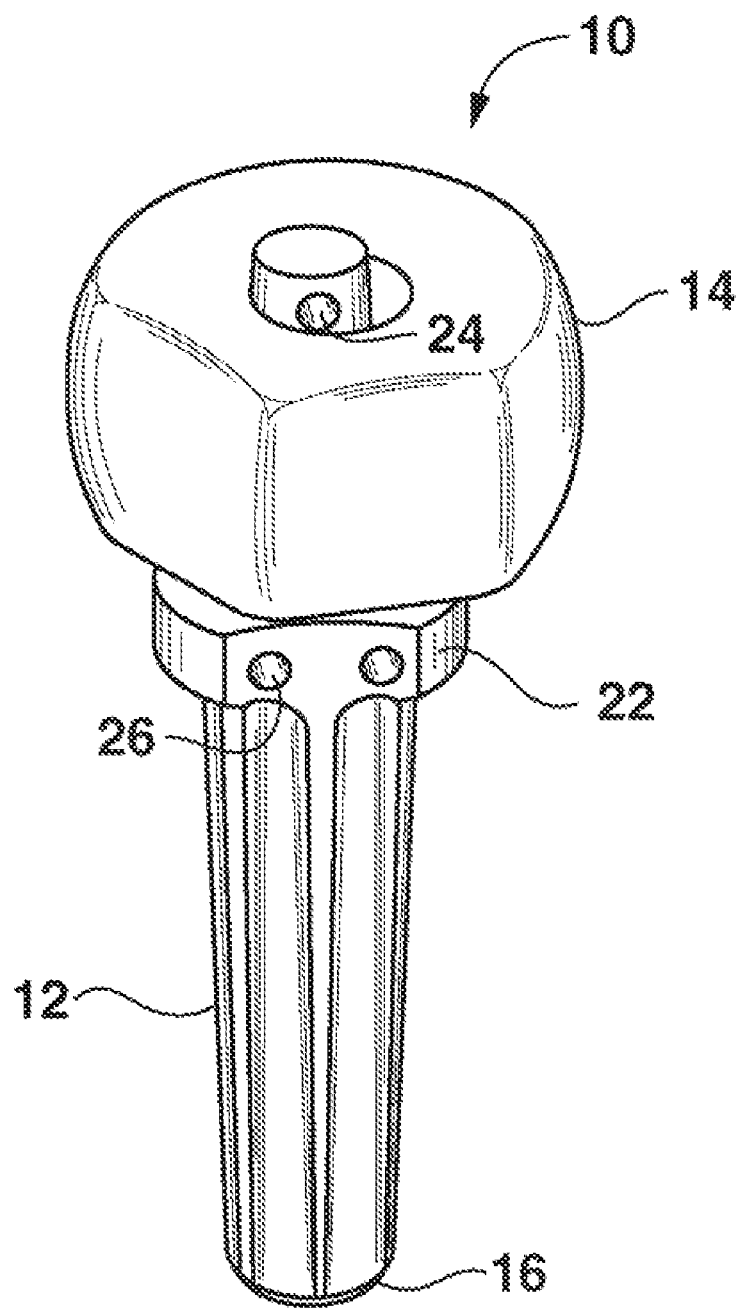
FIG. 1 illustrates an embodiment of a modular ulnar implant in accordance with the present invention.

FIG. 1 illustrates a modular ulnar implant 10 in accordance with the articulating implant system of the present invention. The implant 10 is intended to be an anatomical replacement for the distal ulna after its resection. The modular ulnar implant 10 includes a fixation component and an articulating component. Specifically, the fixation component is a stem 12 and the articulating component is a head 14. Preferably, the stem 12 attaches to the head 14 via a morse taper.

With particular reference to FIG. 1, the stem 12, or fixation component, is elongated and formed with first and second ends, 16 and 18. The first stem end 16 is configured for fixation to a bone, specifically, for insertion into the intramedullary canal of the distal ulna to thereby anchor the modular ulnar implant to the distal ulna. The stem 12 is tapered to match the ulnar canal anatomy and facilitate insertion of the first stem end 16 into the intramedullary canal of the distal ulna. Preferably, the stem 12 is provided with flutes 20 for to prevent rotation of the stem 12 in the intramedullary canal of the distal ulna, thereby facilitating effective fixation of the implant 10 in the canal. The second stem end 18 may be formed with a roughened or porous surface to enable a cement-free joint between the stem and the distal ulna. Alternately, or in addition to such surface, cement may be used to anchor the stem 12 in the intramedullary canal of the distal ulna.

The second stem end 18 is configured for operative attachment to the head 14. The stem 12 includes a platform 22 near the head interface at the second stem end 18 to prevent subsidence into the ulnar canal or excessive penetration of the stem 12 into the intramedullary canal of the distal ulna.

The stem 12 includes, at or near the second stem end 18, suture holes 24 and 26 for receiving sutures to anchor the implant 10 to soft tissues. Sutures threaded through the suture holes 24 and 26 anchor the implant to the triangular soft tissues that are exposed after resection of the distal ulna. These soft tissues include the ulna collateral capsule, the triangular fibrocartilage, and the extensor carpi ulnaris subsheath. A stem extender collar may be used to add additional resection height. The stem 12 may include an instrument interface for positioning control.

Figure 2:
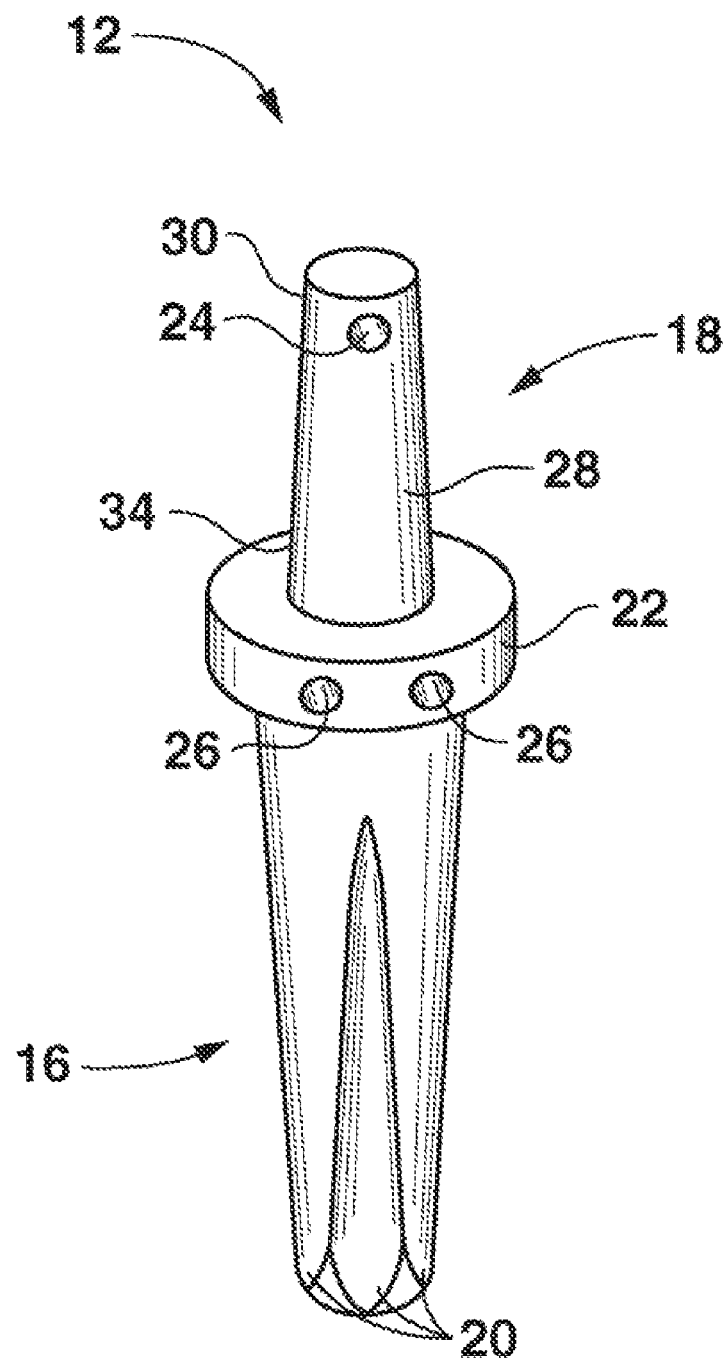
FIG. 2 illustrates the stem of the modular ulnar implant of FIG. 1.

As more clearly seen in FIG. 2, the stem 12 includes an extension 28 at the second end 18, preferably centrally located and formed as a morse taper. The extension 28 is configured for receipt by a bore in the head 14. At least one suture hole 24 is provided at a distal end 30 of the extension 28 for receiving sutures, the suture hole 24 being accessible after the head 14 has been placed on the stem 12. Suture holes 26 may also be provided on the platform 22 near the stem second end 18, near the head interface. In this embodiment, the suture holes 26 and 24 in the platform and in the extension, respectively, anchor the implant 10 to the triangular soft tissues.

Figure 3:
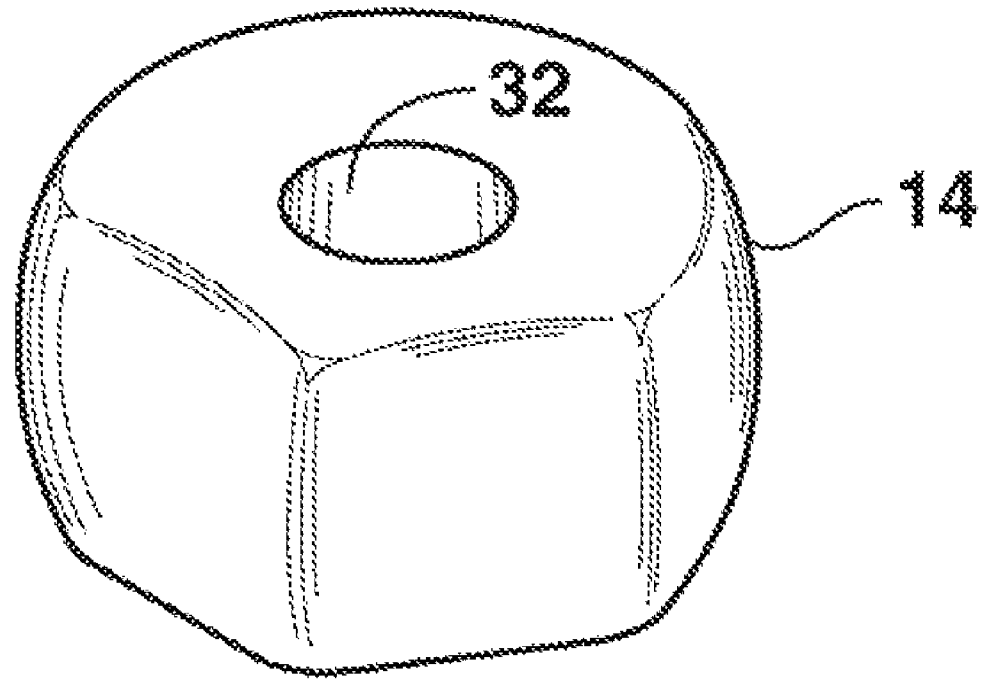
FIG. 3 illustrates the head of the modular ulnar implant of FIG. 1.

The head 14, or articulating component, as shown in FIG. 3, is configured for articulating against bone or cartilage. With reference to FIG. 1, it can be seen that the head 14 is offset from the stem 12 after the implant 10 has been assembled. The head 14 is triangulated to reproduce normal anatomy, and has an approximately 200° arc for mating with the radial sigmoid notch. The head includes a bore 32 extending completely therethrough for receiving an extension from the stem. In alternate embodiments, the head 14 may include a bore extending less than completely therethrough for mating with the second end 18 of the stem 12. Additionally, the head 14 may include a drainage hole and instrument interface on its distal surface to allow effective in vivo assembly and rotational positioning. Optionally, the head 14 is covered, at least near the triangulated portion, with an ingrowth coating, or is otherwise provided with a porous surface, to promote ingrowth with the soft tissues.

The second end 18 of the stem 12 and the bore 32 of the head 14 are complementary so as to provide a secure fit between the head 14 and the stem 12 when the second stem end 18 is inserted in the bore 32 of the head 14. Thus, for example, the bore 32 is provided through the head 14 such that the extension 28 of the stem 12 passes completely therethrough, with both the extension 28 of the stem 12 and the bore 14 being Morse tapers. In the embodiment shown in FIG. 1, insertion of the stem extension 28 through the bore 32 results in the suture hole 24 provided at the distal end 30 of the extension 28 extending through the bore 32 while the suture holes 26 provided at the proximal end of the extension 34 fail to pass through the bore 32. Thus, upon assembly, the implant 10 has suture holes at both ends of the head 14.

Thus, using the modular ulnar implant of the invention, the implant is attached to the soft tissues via the stem (or fixation component). By having the suture attachment means on the fixation component, a stem in a modular ulnar implant system, forces from the suture tissue attachment are transferred directly through the fixation component to the bone and not through the connection of the articulating component to the fixation component. As a result, there is no risk of separation of the head and stem due to biomechanical forces from the tissues attached by suture to the implant.

In order to implant an ulnar implant in accordance with the articulating implant system of the present invention, the distal ulna is first exposed. The distal ulna may be exposed by making an incision along the medial shaft of the distal ulna in line with the ulnar styloid. Alternatively, a dorsal incision centered over the distal radioulnar joint in line with the fourth metacarpal may be used to expose the distal ulna. Once exposed, a template may be placed against the distal ulna and located distally over the articular surface of the distal ulna to mark the prescribed resection length. The distal ulna is resected, by, for example, using an oscillating saw, exposing the intramedullary canal and the soft tissues that formerly surrounded the distal ulna. Once exposed, the intramedullary canal is identified and reamed to accommodate an appropriately sized stem.

Prior to implantation of the ulnar implant, a trial stem and trial head may be used to verify anatomical alignment and to ensure that the proper resection length has been achieved. After removal of the trial stem and trial head, the stem of the stem may be inserted into the intramedullary canal of the distal ulna to anchor the implant to the distal ulna. Specifically, the first end of the stem is inserted into the intramedullary canal, for example by using an impactor until the platform contacts the distal ulna. The fit between the stem and the distal ulna may be assessed by applying a distal traction on the stem. Any movement of the stem in the intramedullary canal of the distal ulna indicates that a firm fit has not been obtained. If a firm fit is not obtained between the stem and the distal ulna after impaction of the stem, a bone cement such as polymethylmethacrylate may be used to cement the stem to the distal ulna.

Once the stem has been secured within the distal ulna, the head may be impacted onto the stem. Specifically, the extension at the second stem end may be inserted into the bore formed in the head. The head may be advanced onto the stem with an impactor until a secure fit is obtained between the head and the stem.

The stem may then be sutured to the soft tissue formerly surrounding the distal ulna, specifically the ulna collateral capsule, the triangular fibrocartilage, and the extensor carpi ulnaris subsheath using the suture holes formed in the stem. Non-absorbable sutures may be used. By having the sutures attach to the implant through the fixation component, forces from the suture tissue attachment are transferred directly through the fixation component to the bone, thereby reducing or eliminating the risk of component separation due to such forces. After the head is attached to the stem and the stem has been sutured to the soft tissue, the sutures may be tied into the capsular sleeve surrounding the implant and the subcutaneous tissues and skin may be closed over the implant.

While a preferred embodiment of the present invention has been described, it should be understood that various changes, adaptations, and modifications may be made therein without departing from the spirit of the invention and the scope of the appended claims.

The invention claimed is:

1. An ulnar implant for replacing the distal ulna after resection of the distal ulna, wherein the resection exposes soft tissue formerly in contact with the distal ulna, the implant comprising:
   an elongated stem having first and second ends, the first end being sized and configured for insertion into the intramedullary canal of the distal ulna, the second end being configured for attachment to a head, wherein suture holes are provided at or near the second end for receiving sutures attaching the implant to the soft tissue;
   a head, said head being a separate component from said stem, said head having a triangulated portion when viewed from a distal end to substantially mimic normal anatomy, the head being configured for mating with the sigmoid notch of the distal radius, and the head further being configured for attachment to the second end of the stem.

2. The implant of claim 1, further including a platform at or near the second end of the stem, the platform being configured to prevent subsidence into the ulnar canal.

3. The implant of claim 2, wherein the suture holes are provided through the platform.

4. The implant of claim 1, further including an extension extending from the second end of the stem, the extension having proximal and distal ends, one of the suture holes being provided at a distal end of the extension.

5. The implant of claim 4, wherein the head includes a bore extending completely therethrough for receiving the extension from the stem, the extension of the stem being configured such that the distal end of the extension extends completely through the bore.

6. The implant of claim 5, wherein the extension and the bore are Morse tapers.

7. The implant of claim 4, further including a platform configured to prevent subsidence into the ulnar canal, the platform being positioned at or near the proximal end of the extension.

8. The implant of claim 7, wherein the suture holes are provided through the platform and through the distal end of the extension.

9. The implant of claim 1, wherein the head includes a 200 degree arc for mating with the radial sigmoid notch.

10. The implant of claim 1, wherein at least a portion of the head is covered with an ingrowth coating at least near the triangulated portion to promote ingrowth with the soft tissues.

11. The implant of claim 1, wherein the stem includes flutes at its first end to prevent rotation of the stem in the intramedullary canal of the distal ulna.

12. An ulnar implant for replacing the distal ulna after resection of the distal ulna, wherein the resection exposes soft tissue formerly in contact with the distal ulna, the implant comprising:
   an elongated stem having first and second ends, the first end being sized and configured for insertion into the intramedullary canal of the distal ulna, the second end being configured for attachment to a head;

an extension extending from the second end of the stem, the extension having proximal and distal portions and ends, a suture hole being provided in the distal portion of the extension;

a platform configured to prevent subsidence of the stem into the ulnar canal, the platform being positioned at or near the proximal end of the extension, wherein suture holes are provided through the platform; and a head, said head being a separate component from said stem, the head having a triangulated portion when viewed from a distal end to mimic normal anatomy, the head being configured for mating with the sigmoid notch of the distal radius, and the head including a bore extending completely therethrough for receiving the extension from the stem, the extension of the stem being configured such that the distal end of the extension extends completely through the bore.

13. The implant of claim 12, wherein the head includes a 200 degree arc for mating with the radial sigmoid notch.

14. The implant of claim 12, wherein at least a portion of the head is covered with an ingrowth coating at least near the triangulated portion to promote ingrowth with the soft tissues.

15. The implant of claim 12, wherein the stem includes flutes at its first end to prevent rotation of the stem in the intramedullary canal of the distal ulna.

16. A method for implanting a modular ulnar implant in a patient, the method comprising the steps of:

exposing and resecting the distal ulna of the patient to expose the intramedullary canal of the ulna and the soft tissue that formerly surrounded the distal ulna;

providing an elongated stem having first and second ends, the first end being sized and configured for insertion into the intramedullary canal of the distal ulna, the second end being configured for attachment to a head, wherein suture holes are provided at or near the second end for receiving sutures attaching the implant to the soft tissue;

providing a head, the head having a triangulated portion when viewed from a distal end, the head configured for mating with the sigmoid notch of the distal radius, and the head further being configured for attachment to the second end of the stem;

inserting the stem into the intramedullary canal of the distal ulna;

suturing the stem to the soft tissue formerly surrounding the distal ulna; and attaching the head to the stem.

17. The method of claim 16, wherein non-absorbable sutures are used to suture the stem to the soft tissue formerly surrounding the distal ulna.

18. The method of claim 16, wherein the stem is sutured to the ulnar collateral capsule.

19. The method of claim 16, wherein the stem is sutured to the triangular fibrocartilage.

20. The method of claim 16, wherein the stem is sutured to the extensor carpi ulnaris subsheath.

* * * * *